US008222454B2

(12) United States Patent
Ai et al.

(10) Patent No.: US 8,222,454 B2
(45) Date of Patent: Jul. 17, 2012

(54) PROCESS FOR PREPARING OPTICAL PURE MILNACIPRAN AND ITS PHARMACEUTICALLY ACCEPTED SALTS

(75) Inventors: Lin Ai, Chengdu (CN); Xiao Liu, Sichuan (CN)

(73) Assignee: Zhejiang Haisen Pharmaceutical Co., Ltd., Dongyang (CN)

( * ) Notice: Subject to any disclaimer, the term of this patent is extended or adjusted under 35 U.S.C. 154(b) by 456 days.

(21) Appl. No.: 12/517,379

(22) PCT Filed: Nov. 28, 2007

(86) PCT No.: PCT/CN2007/071142
§ 371 (c)(1),
(2), (4) Date: Jun. 3, 2009

(87) PCT Pub. No.: WO2008/067752
PCT Pub. Date: Jun. 12, 2008

(65) Prior Publication Data
US 2010/0016636 A1 Jan. 21, 2010

(30) Foreign Application Priority Data
Dec. 4, 2006 (CN) .......................... 2006 1 0022397

(51) Int. Cl.
*C07C 233/58* (2006.01)
(52) U.S. Cl. ...................................... 564/190; 564/164
(58) Field of Classification Search .................. 564/164, 564/190
See application file for complete search history.

(56) References Cited

U.S. PATENT DOCUMENTS
7,659,305 B2 * 2/2010 Rawson ........................ 514/423
2006/0247291 A1 * 11/2006 Graham et al. ............... 514/400

FOREIGN PATENT DOCUMENTS
CN 1699332 A 11/2005
WO WO 2006/080555 A1 3/2006

OTHER PUBLICATIONS
Shuto et al, Tetrahedron Letters, vol. 37, No. 5, 641-644, 1996.*

* cited by examiner

*Primary Examiner* — Shailendra Kumar
(74) *Attorney, Agent, or Firm* — Mei & Mark LLP

(57) ABSTRACT

The present invention discloses a process for preparing optically pure milnacipran and their pharmaceutically acceptable salts, which adopts racemic milnacipran as starting material, tartaric acid derivatives and their compositions as resolving agents to resolve.

9 Claims, 2 Drawing Sheets

PROCESS FOR PREPARING OPTICAL PURE MILNACIPRAN AND ITS PHARMACEUTICALLY ACCEPTED SALTS

This application is a 371 of PCT/CN07/71142, filed Nov. 28, 2007.

TECHNICAL FIELD

This invention relates to a process for the preparing optically pure milnacipran or milnacipran enriched with specified configuration, or their salts.

BACKGROUND OF THE INVENTION

Milnacipran (the trade name is Ixel, and the chemical name is 1-phenyl-2-(aminomethyl)cyclopropane-N,N-diethyl carboxamide) is a antidepressant which is developed by FABRE MEDICAMENT SA PIERRE and is launched in 1997. It is reported that said drug is also used to treat fatigue, pain, fibromyalgia, Irritable bowel syndrome and the like. At present, it is mostly sold in the form of milnacipran hydrochloride. Milnacipran belongs to dual inhibitors of serotonin and norepinephrine reuptake (SNRI), which is the fourth generation antidepressant and can can inhibit both of serotonin and norepinephrine reuptake, with similar action strength. It is mainly useful to treat depression, especially major depression. There are 22 countries approved milnacipran for treating depression at present. Among of the antidepressants, milnacipran has the similar efficacy as TCAs and SSRIs, less drugs interaction, obviously less adverse reaction than TCAs, and less adverse reaction than SSRIs in some aspects, and when comparing with SSRIs, it has the similar efficacy, but more quickly in taking effect, the time of taking effect of which is about two weeks, due to milnacipran's ability of plasma protein-binding is lower and unsaturated, and without metabolism through the cytochrome P450 system, this means the medication is not likely to interact with other medications. Because milnacipran's half-life is relatively shorter, it have advantage of no residual effect after treatment, therefore it has fine tolerance and security.

The structural formula of milnacipran hydrochloride is as follows:

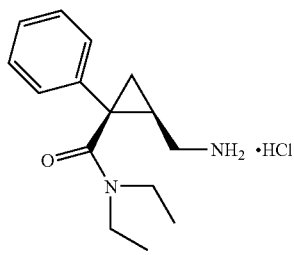

In 1992, a resolution had been approved by American Food and Drug Administration (FDA) and The European Committee for Proprietary Medicinal Products, which encouraged drugs with chiral center were in optically pure form for marketing authorization; in 1996, a project had been proposed by FDA that drugs with chiral center must be in optically pure form when it is applying for marketing authorization. There are two chiral center in the molecular structure of milnacipran, it should be two group of enantiomers-four compounds in theory. Due to the molecular configuration, the cis-isomer is the mainly synthetic product, that exist in two forms of optically enantiomers: the dextrogyral enantiomer of cis-milnacipran hydrochloride Z-(1 S,2R) and the levogyral enantiomer of cis-milnacipran hydrochloride Z-(1R,2S). The US patent US 2004/0162334, US 20060014837 and Chinese patent CN 1699332A have carried out detailly research on the single enantiomer of milnacipran, and the result indicates that the dextrogyral enantiomer of milnacipran hydrochloride had activity which was significantly higher than racemic milnacipran, with less risk of cardiovascular disturbances and tissue and organ organic toxicity.

The molecular structural formula of the two chiral enantiomers of milnacipran hydrochloride are as follows:

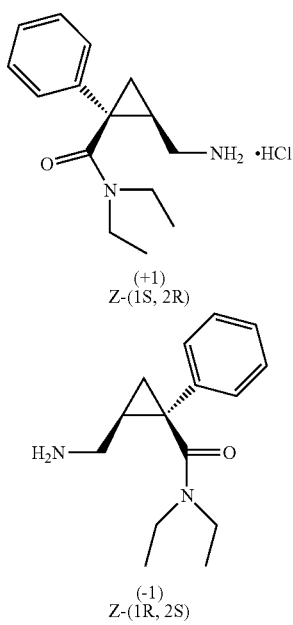

At present, the method for preparing optically pure milnacipran is mostly the asymmetric synthesis method, Bonnaud et al. resolved racemic γ-butyrolactone (1-phenyl-3-oxa-bicyclo[3.1.0]hexane-2-ketone) as starting material by R-(+)-phenyl ethylamine, the obtained optically active γ-butyrolactone was separated by chiral stationary phase method, then by which as intermediate target product could be synthesized (Bonnaud et al., 1985, Journal of Chromatography, Vol. 318: 398-403); Shuto, S. et al. adopted optically epichlorohydrin and benzacetonitril as starting material, the optically fused γ-butyrrolactone was obtained by hydrolysis after nucleophilic substitution is performed twice in the presence of sodium amide. Then the ring of γ-butyrrolactone was opened to liberate hydroxyl group, substituted by azide group, reduced to give (+) and (−)-milnacipran (Shuto et al., Tetrahedron letters, 1996 Vol. 37: 641-644); Grard et al. separated racemic milnacipran to give optically pure milnacipran as well by high performance capillary electrophoresis chirality mehod. (Grard et al., 2000, Electrophoresis 21: 3028-3034); Doyle and Hu adopt phenylacetic acid as starting material, optically pure milnacipran can be obtained after asymmetric catalysis (Doyle and Hu, 2001, Advanced Synthesis and Catalysis, Vol. 343: 299-302). In a word, both of the asymmetric synthesis method and the chromatography method can give optically pure milnacipran with higher e.e.value (enantiomeric excess), but with complex operation and high cost.

DISCLOSURE OF THE INVENTION

The object of the invention is to provide a new process for preparing optically pure milnacipran with higher optically pure, it has not only better yield, simple process and low cost, but also can obtained two kinds of configurational optically pure milnacipran.

The object of the invention is achieved by technical solutions as follows.

The inventior adopts racemic milnacipran as starting material, and the optically pure resolving agents in the molar ratio of 1:0.5-1.5 are dissolved in ketone or alcohol solvent, and mixed, then crystallization is performed and filtered to give the resolved product; the obtained resolved product is suspended in organic solvent and water, then, alkali is added to the suspended milnacipran to separate out specially free alkali of optically pure milnacipran, and the free alkali is reacted with an acid to obtain corresponding salt of milnacipran.

In the above embodiments, the resolving agents (split reagent) used is tartaric acid derivatives and their compositions, wherein (−)-milnacipran is resolved by L-(−)-tartaric acid derivatives or their compositions; (+)-milnacipran is resolved by D-(+)-tartaric acid derivatives or their compositions.

The molecular structural of tartaric acid derivatives and their compositions are as follows:

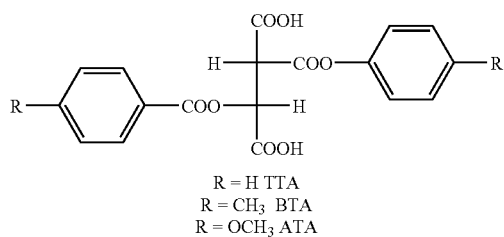

R = H TTA
R = CH₃ BTA
R = OCH₃ ATA

A group T of resolving agents (split reagent) is composed of: di-p-toluoyl tartaric acid, di-p-methoxybenzoyl tartaric acid and di-benzoyl tartaric acid;

A group T1 of resolving agents (split reagent) is composed of: di-p-methoxybenzoyl tartaric acid and di-p-toluoyl tartaric acid;

A group T2 of resolving agents (split reagent) is composed of: di-p-toluoyl tartaric acid and di-benzoyl tartaric acid;

A group T3 of resolving agents (split reagent) is composed of: di-p-methoxybenzoyl tartaric acid and di-benzoyl tartaric acid.

In the above embodiments, the resolved product formed by the rotation-mixed (racemic) milnacipran and the resolving agents (split reagent) can be recrystallized in ketone or alcohol solvent to obtain product with more higher optically purity; and which can also be separated out to obtain free alkali of optically pure milnacipran, then resolution is performed two or more times to purify.

In the above embodiments, the ketone or alcohol solvent used is ethanol, isopropanol, propanone, butanone or their mixed aqueous solution.

In the above embodiments, the acid used is hydrochloric acid, hydrobromic acid, sulfuric acid or phosphoric acid and like; the alkali used is sodium carbonate, potassium carbonate, sodium hydroxide, potassium hydroxide and their aqueous solution.

In the above embodiments, the organic solvent is one of ethyl acetate, ethyl ether, dichloromethane, petroleum ethern or their mixture.

The invention makes use of methods of resolution with single resolving agent or with combination of the resolving agents to prepare optically pure milnacipran, which has not only overcome some shortcomes of the asymmetric synthesis method and the chromatography method, but also easily obtained two kinds of chiral enantiomers of milnacipran, and both of the e.e. valve and the chemical purity can reach more than 99.0%, the total yield of resolution can reach 50-65%. The present method has low cost, is easy to operate, is suitable for industrial scale production, has prodigious use value.

DETAILED DESCRIPTION OF THE INVENTION

Figure 1:
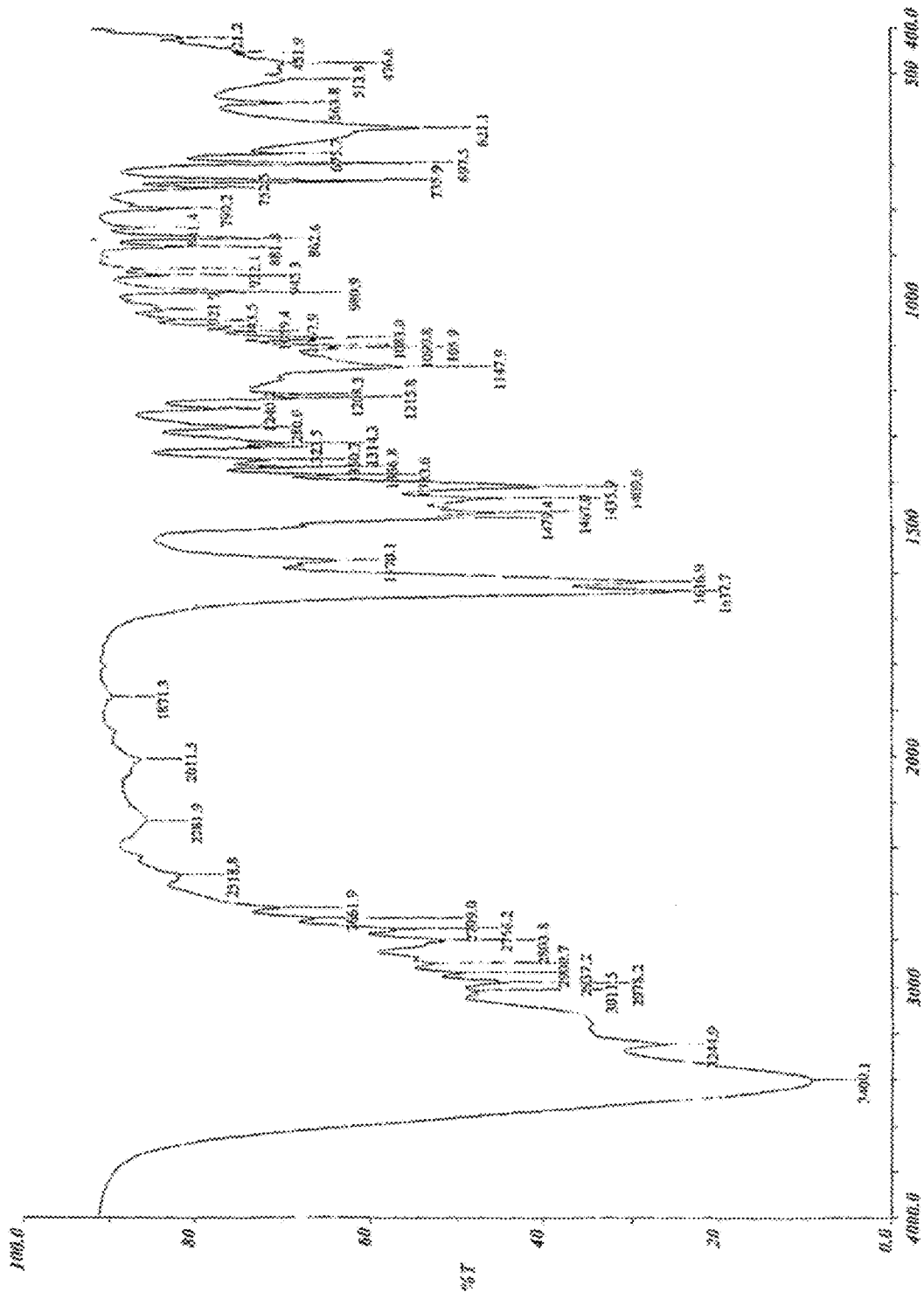
FIG. 1 is the infared spectrum of (+)-milnacipran hydrochloride.
Figure 2:
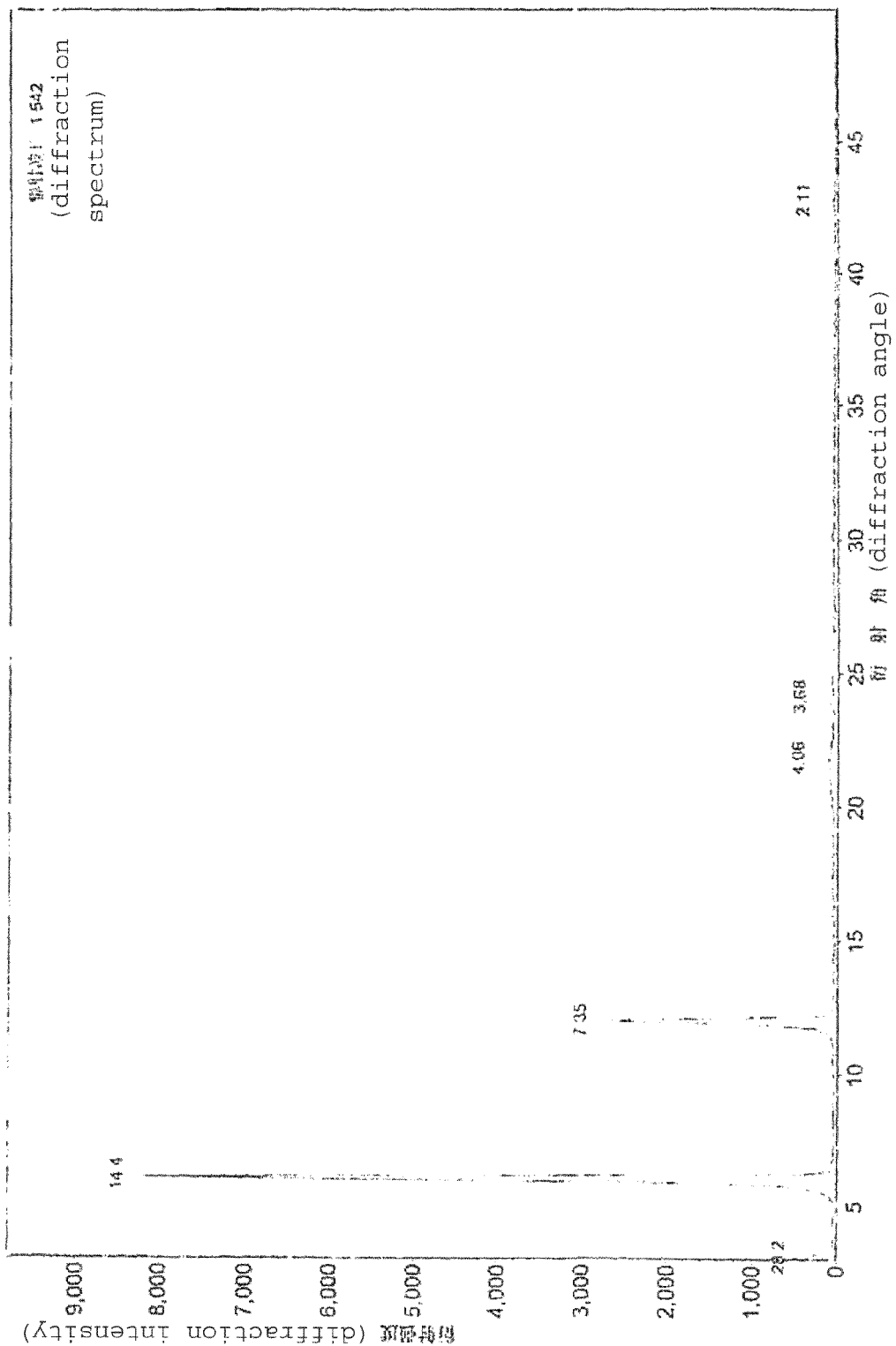
FIG. 2 is the X-ray diffraction pattern of (+)-milnacipran hydrochloride.

The invention will be described in detail by examples.

Example 1

Resolution of Rotation-Mixed (Racemic) Milnacipran by the Group T1 of D-Resolving Agents (Split Reagent)

1.000 g (3.53 mmol) of racemic milnacipran hydrochloride is suspended in the mixture of 10 ml of aqueous solution and 10 ml of dichlormethane, and 10% sodium hydroxide aqueous solution is added under stirring until the aqueous phase is basic (pH=11). The organic phases is separated, the aqueous phase is extracted with dichlormethane (8 ml every time) three times, the organic extracts are combined, washed two times with saturated salt water, then dried with anhydrous sodium sulfate, filtered and removed dichlormethane by distillation to give racemic milnacipran freebase. The racemic milnacipran freebase obtained and 1.420 g (3.53 mmol) of the group T1 of D-resolving agents are dissolved in 45 ml of 98% acetone-water respectively, mixed and crystallized, filtered to afford 1.054 g of resolved product formed by (+)-milnacipran and the group T1 of D-resolving agents, 80.1% yield, the optical purity of (+)-milnacipran contained in which is 98.5% e.e.

Example 2

Resolution of Rotation-Mixed (Racemic) Milnacipran by D-di-p-methoxybenzoyl Tartaric Acid 1.000 g (3.53 mmol) of rotation-mixed (racemic) milnacipran hydrochloride is changed to racemic milnacipran freebase following the method of example 1. The racemic milnacipran obtained and 1.773 g (4.24 mmol) of D-di-p-methoxybenzoyl tartaric acid are dissolved in 100 ml of 98% acetone-water respectively, mixed and crystallized, filtered to afford 0.923 g of resolved product formed by (+)-milnacipran and D-di-p- methoxybenzoyl tartaric acid, 70.1% yield, the optical purity of (+)-milnacipran contained in which is 89.9% e.e.

Example 3

Resolution of Rotation-Mixed (Racemic) Milnacipran by the Group T of L-Resolving Agents (Split Reagent)

1.000 g (3.53 mmol) of rotation-mixed (racemic) milnacipran hydrochloride is changed to racemic milnacipran freebase following the method of example 1. The racemic milnacipran obtained and 1.402 g (3.53 mmol) of the group T of L-resolving agents (split reagent) are dissolved in 45 ml of 98% acetone-water respectively, mixed and crystallized, filtered to afford 1.094 g of resolved product formed by (−)-milnacipran and the group of L-resolving agents (split reagent), 83.1% yield, the optical purity of (−)-milnacipran contained in which is 69.9% e.e.

Example 4

Resolution of Rotation-Mixed (Racemic) Milnacipran by L-di-p-toluoyl Tartaric Acid 1.000 g (3.53 mmol) of rotation-mixed (racemic) milnacipran hydrochloride is changed to racemic milnacipran following the method of example 1. The racemic milnacipran obtained and 1.624 g (3.53 mmol) of L-di-p-di-p-toluoyl tartaric acid are dissolved in 45 ml of 98% isopropyl alcohol-water respectively, mixed and crystallized, filtered to afford 0.831 g of resolved product formed by (−)-milnacipran and L-di-p-toluoyl tartaric acid, 63.1% yield, the optical purity of (−)-milnacipran contained in which is 73.1% e.e.

Example 5

Recrystallization of Resolved Product Formed by (+)-Milnacipran and D-di-p-methoxybenzoyl Tartaric Acid 0.923 g of the resolved product formed by (+)-milnacipran and D-di-p-toluoyl tartaric acid from example 2 is dissolved in 20 ml of 98% isopropyl alcohol, the mixture is then cooled gradually to room temperature, filtered to afford resolved product formed by (+)-milnacipran and D-di-p-methoxybenzoyl tartaric acid, 80.3% yield, the optical purity of (+)-milnacipran contained in which is 96.7% e.e.

Example 6

Salt Formation of (+)-milnacipran 1.054 g of the resolved product obtained by (+)-milnacipran and the group T1 of D-resolving agents (split reagent) is suspended in the mixture of 50 ml of aqueous solution and 50 ml of dichlormethane, mixed thoroughly, and 10% sodium hydroxide aqueous solution is added under stirring until the aqueous phase is basic (pH=11). The organic phases is separated, the aqueous phase is extracted with dichlormethane (30 ml every time) three times, the organic extracts are combined, washed two times with saturated solution of sodium chloride, then dried with anhydrous sodium sulfate, filtered and evapourated to dryness. The free alkali of (+)-milnacipran is afforded, 95.8% yield.

The free alkali is dissolved in absolute alcohol, the mixture is adjusted to pH≦3 by the solution of absolute alcohol in hydrogen chloride, evapourated to give remainder whose weight is 2-3 times the weight of the free alkali under reduced pressure, then diethyl ether is added and a lot of crystal is precipitated, which is kept in the refrigerating chamber of refrigerator overnight, filtered and dried under infrared lamp to give 0.434 g of (+)-milnacipran hydrochloride, 84.6% yield of salt formation. $[a]D25=+79.1$ (C=0.98, CHCl3), Mp.: 182.2-183.2□. optical purity: 100% e.e.°

(reference: mp:176-178□ $[a]D25=+72.8$ (c=0.95, CHCl3)) $^1$H-NMR (400 MHz, CDCl3) 0.893 (3H, t) 1.103 (4H, t), 1.749 (1H, m), 1.844 (1H, m), 2.453 (1H, m), 3.354 (4H, m), 3.736 (1H, m), 7.189 (2H, m), 7.182 (1H, m). 13C-NMR (400 MHz, CDCl3) 12.932, 12.179, 17.986, 25.360, 34.647, 42.956, 39.557, 41.929, 125.707, 127.151, 128.868, 138.267, 170.583. IR (KBr) 735.0 (mono-substituted by benzene ring), 1148.1 (tertiary amine), 1465.9 (—CH3), 1614.9 (—CO(NH)—), 1637.8 (bending vibration of —NH2), 2936.2 (—CH2-), 2977.6 (cyclopropane), 3010.6 (benzene ring), 3400.2 (—NH2). HR-MS (EJ) calcd for C15H22N2O 246.32, found 246.1 (free alkali). X-ray diffraction spectrum (expressed by 2θ angle and interplanar spacing (dvalue):0.0 (28.2), 6.0 (14.4), 12.0 (7.35), 21.3 (4.1), 24.0 (3.68) and 42.8 (2.11).

What is claimed is:

1. A process for preparing optically pure milnacipran and its pharmaceutically acceptable salts, comprising the steps of:
    adopting racemic milnacipran as a raw material;
    adopting at least one of a tartaric acid derivative or its composition as resolving agent;
    dissolving and mixing the raw material with the resolving agent in the molar ratio of 1:0.3-1.3 in ketone or alcohol solvent to produce a mixture;
    crystallizing the mixture under room temperature to precipitate diastereoisomer salt as a solid;
    filtering to obtain a resolved product;
    suspending the resolved product in organic solvent and water to produce a suspended mixture;
    adding alkali to the suspended mixture to separate out free alkali of optically pure milnacipran; and
    reacting the free alkali of optically pure milnacipran with an acid to obtain its corresponding salt.

2. The process according to the claim 1, wherein:
    (−)-milnacipran is resolved by at least one of L-(−)-tartaric acid derivatives or their compositions;
    (+)-milnacipran is resolved by at least one of D-(+)-tartaric acid derivatives or their compositions; and
    milnacipran of at least one other configuration is separated out from the mixture as enriched raw material.

3. The process according to the claim 1, wherein the resolved product formed by the raw material and the resolving agent can be recrystallized in ketone or alcohol solvent to obtain a product with high optical purity.

4. The process according to the claim 1, wherein the resolved product formed by the raw material and the resolving agent is separated out to obtain free alkali of optically pure milnacipran, then resolution is performed two or more times to obtain a product with high optical purity.

5. The process according to the claim 1, wherein the ketone or alcohol solvent is ethanol, isopropanol, propanone, butanone or an aqueous solution thereof, or one or more of a mixed solution thereof or a mixed aqueous solution thereof.

6. The process according to the claim 1, wherein the acid is hydrochloric acid, hydrobromic acid, sulfuric acid or phosphoric acid; and wherein the alkali is at least one of sodium carbonate, potassium carbonate, sodium hydroxide, potassium hydroxide or an aqueous solution thereof.

7. The process according to the claim 1, wherein the organic solvent is one of ethyl acetate, ethyl ether, dichloromethane, petroleum ether or a mixture thereof.

8. The process according to claim 1, wherein the resolving agent comprises one or more of di-p-toluoyl tartaric acid, di-p-methoxybenzoyl tartaric acid, di-benzoyl tartaric acid, di-p-toluoyl tartaric acid, or an isomer thereof.

9. The process according to claim 1, wherein the at least one resolving agent has a structure according to:

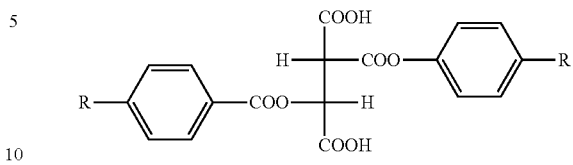

where:
R=H yields TTA;
R=CH$_3$ yields BTA; and
R=OCH$_3$ yields ATA.

* * * * *